United States Patent
Janssen et al.

(10) Patent No.: US 6,803,447 B2
(45) Date of Patent: Oct. 12, 2004

(54) PREPARATION OF SUPRAMOLECULAR POLYMERS BY COPOLYMERIZATION OF MONOMERS CONTAINING QUADRUPLE HYDROGEN BONDING UNITS WITH REGULAR MONOMERS

(75) Inventors: Henricus Marie Janssen, Eindhoven (NL); Gaby Maria Leonarda Van Gemert, Montfort (NL); Aafke Tessa Ten Cate, Den Bosch (NL); Dimphna Johanna Maria Van Beek, Eindhoven (NL); Rintje Pieter Sijbesma, Den Bosch (NL); Egbert Willem Meijer, Waalre (NL); Anton Willem Bosman, Eindhoven (NL)

(73) Assignee: Eutechpark MMP1.28, Eindhoven (NL)

( * ) Notice: Subject to any disclaimer, the term of this patent is extended or adjusted under 35 U.S.C. 154(b) by 0 days.

(21) Appl. No.: 10/224,554

(22) Filed: Aug. 21, 2002

(65) Prior Publication Data

US 2004/0034190 A1 Feb. 19, 2004

Related U.S. Application Data

(60) Provisional application No. 60/403,636, filed on Aug. 16, 2002.

(51) Int. Cl.$^7$ .................. C08F 2/00; C07D 239/00; C08G 63/00
(52) U.S. Cl. .................. 528/423; 528/363; 528/422; 528/310; 528/272; 528/44; 526/72; 526/75; 540/1; 544/1; 524/452; 525/278; 525/279; 525/281; 525/327.2
(58) Field of Search ................. 528/310, 422, 528/272, 363, 44, 423, 183, 172, 229, 315, 327; 526/72, 75; 525/278–281, 327.2, 92 A, 329.4, 329.5; 524/452; 544/1; 540/1

(56) References Cited

U.S. PATENT DOCUMENTS

| 4,216,318 | A | * | 8/1980 | Brown et al. ............... 544/310 |
| 5,610,268 | A | * | 3/1997 | Meijer et al. ............... 528/363 |
| 5,736,535 | A | * | 4/1998 | Bernstein et al. ............ 514/64 |
| 6,320,018 | B1 | | 11/2001 | Sijbesma et al. | |

OTHER PUBLICATIONS

Hirschberg et al., J.H.K., "Supramolecular Polymers from Linear Telechelic Siloxanes with Quadruple–Hydrogen–Bonded Units," *Macromolecules* 1999, vol. 32, pp. 2696–2705.

Lange, F.M. et al., "Supramolecular Polymer Interactions Based on the Alternating Copolymer of Styrene and Maleimide," Macromolecules 1995, vol. 28, pp. 782–783.

Lee et al., R. "Polymerization of Ureidopyrimidinone–Functionalized Olefins by Using Late–Transition Metal Ziegler–Natta Catalysts: Synthesis of Thermoplastic Elastomeric Polyolefins," *Angew. Chem. Int. Ed.* 2001, vol. 40, No. 11, pp. 2153–2156.

Yamauchi, Koji, et al., Abstract of "Synthesis And Characterization Of Novel Multiple–Hydrogen Bonded Macromolecules Via a Michael Reaction," Dept. of Chemistry, Virginia Polytechnic Institute and State University.

* cited by examiner

Primary Examiner—P. Hampton Hightower
(74) Attorney, Agent, or Firm—Katten Muchin Zavis Rosenman (57) ABSTRACT

The invention relates to the synthesis of polymers containing self-complementary quadruple hydrogen groups by copolymerizing monomers containing a quadruple hydrogen bonding group with one or more monomers of choice. The resulting polymers show unique new characteristics due to the presence of additional physical interactions between the polymer chains that are based on multiple hydrogen bonding interactions (supramolecular interactions).

24 Claims, 1 Drawing Sheet

*Figure 1: Solution viscosities of PMMA solutions in chloroform at 20 °C.*

PREPARATION OF SUPRAMOLECULAR POLYMERS BY COPOLYMERIZATION OF MONOMERS CONTAINING QUADRUPLE HYDROGEN BONDING UNITS WITH REGULAR MONOMERS

FIELD OF THE INVENTION

The invention relates to the synthesis of polymers containing self-complementary quadruple hydrogen groups by copolymerizing monomers containing a quadruple hydrogen bonding group with one or more monomers of choice. The resulting polymers show unique new characteristics due to the presence of additional physical interactions between the polymer chains that are based on multiple hydrogen bonding interactions (supramolecular interactions).

BACKGROUND OF THE INVENTION

This invention relates to polymers containing units that are capable of forming H-bridges with each other leading to physical interactions between different polymer chains. The physical interactions originate from multiple hydrogen bonding interactions (supramolecular interactions) between self-complementary units containing at least four hydrogen bonds (units capable of forming at least four hydrogen bonds are in this application abbreviated as 4H-units or 4H-monomers and are used in this application as interchangeable terms) in a row. Sijbesma et al. (U.S. Pat. No. 6,320,018; Science, 278, 1601) discloses such self-complementary units which are based on 2-ureido-4-pyrimidones. In Example X the 4H-unit 6-(3-butenyl)-2-butylureido-4-pyrimidone is disclosed. Polymers obtained by polymerization of the carbon—carbon double bond moiety of this compound are, however, not disclosed.

Telechelic polymers have been modified with 4H-units (Folmer, B. J. B. et al., Adv. Mater. 2000, Vol. 12, 874; Hirschberg et al., Macromolecules 1999, Vol. 32, 2696). However, this has been performed after polymerization in a laborious post-modification process. Another drawback of these polymers containing 4H-units is that they only contain the 4H-unit coupled at the ends of the polymers. Consequently, the number of end groups is therefore limited by the amount of end groups (normally 2), and the functional units are always located on the periphery of the polymer.

Polymers containing hydrogen bonding groups in the main chain synthesized via copolymerization of hydrogen bonding monomers have been obtained with hydrogen bonding units containing three H-bonds in a row (Lange F. M. et al., Macromolecules 1995, Vol 28, 782). However, only an alternating copolymer of styrene and maleimide can be used in this approach, and moreover, the H-bonding interactions between the polymers are much weaker than the H-bonding based on the 4H-units, obviously resulting in poorer material properties.

Polymers with quadruple H-bonding units in the main chain have been obtained by copolymerizing 4H-monomers in the main chain of a polyolefin (Coates, G. W. et al., Angew. Chem. Int. Ed., 2001, Vol. 40, 2153). However, complex chemistry has to be used to prepare and to polymerize the monomer and, due to the intrinsic sensitivity of the catalyst needed to obtain the polymer, severe limitations hinder the general use of this system and limits it to tailor-made polyolefin systems. For example, Coates et al. discloses the copolymerization of 1-hexene and a 6-hexenyl-2-ureido-4-pyrimidone derivative with a Ziegler-Natta type nickel based catalyst and diethylaluminum chloride as cocatalyst.

The present invention discloses a convenient synthesis and convenient copolymerization of monomers containing a 4H-unit with other widely available monomers. The present invention can be used for the preparation of a wide range of polymers with 4H hydrogen bonding units in order to provide these polymers with unique new material properties as a result of the incorporation of the 4H-units. These new material properties result from the reversible nature of H-bonding interactions between the polymer chains that allow reversible changing of the material properties by external stimuli like heat or dilution. Consequently, it becomes possible to prepare materials that combine the mechanical properties of conventional macromolecules with the low melt viscosity of organic compounds.

SUMMARY OF THE INVENTION

The invention relates to monomers comprising (a) a monomeric unit having a group that can be polymerized (or a monomeric unit having a polymerizable group), (b) a linking moiety and (c) a structural element capable of forming at least four hydrogen bridges, preferably four hydrogen bridges, wherein the monomer has the general structure:

(a)-(b)-(c).

The invention further relates to processes for the preparation of these monomers, copolymers comprising these monomers and processes for the preparation of these copolymers.

DETAILED DESCRIPTION OF THE INVENTION

Description of the Monomer Containing the 4H-Unit

The monomer containing the 4H-unit comprises a group that can be polymerized, a linker and a 4H-unit. In particular, the group that can be polymerized is linked to a 4H-unit via a linker as is shown below in schematic form.

According to the invention, the monomers comprise (a) a monomeric unit having a group that can be polymerized (i.e. a monomeric unit having a polymerizable group), (b) a linking moiety and (c) a structural element capable of forming at least four hydrogen bridges, preferably four hydrogen bridges, wherein the monomer has the general structure:

(a)-(b)-(c)

Preferably, (a) comprises monomeric units having an ethylenically unsaturated group or an ion-polymerizable group. Most preferably, group (a) comprises monomeric units having an ethylenically unsaturated group.

In general, the structural element that is capable of forming at least four hydrogen bridges has the general form (1') or (2'):

(1')

(2')

If the structural element (c) is capable of forming four hydrogen bridges which is preferred according to the invention, the structural element (c) has preferably the general form (1) or (2):

(1)

(2)

In all general forms shown above the C—$X_i$ and C—$Y_i$ linkages each represent a single or double bond, n is 4 or more and $X_1 \ldots X_n$ (=$X_i$) represent donors or acceptors that form hydrogen bridges with the H-bridge-forming monomer containing a corresponding structural element (2) linked to them, with $X_i$ representing a donor and Y, an acceptor or vice versa. Properties of the structural element having general forms (1'), (2'), (1) or (2) are disclosed in U.S. Pat. No. 6,320,018 which for the US practice is incorporated herein by reference.

The structural elements (c) have at least four donors or acceptors, preferably four donors or acceptors, so that they can in pairs form at least four hydrogen bridges with one another. Preferably the structural elements (c) have at least two successive donors, followed by at least two acceptors, preferably two successive donors followed by two successive acceptors, preferably structural elements according to general form (1') or more preferably (1) with n=4, in which $X_1$ and $X_2$ both represent a donor or an acceptor, respectively, and $X_3$ and $X_4$ both an acceptor or a donor, respectively. According to the invention, the donors and acceptors are preferably O, S, and N atoms.

Molecules that can be used to construct the structural element (c) are nitrogen containing compounds that are reacted with isocyanates or thioisocyanates, or that are activated and reacted with primary amines, to obtain a urea moiety that is part of the quadruple hydrogen bonding site. The nitrogen containing compound is preferably an isocytosine derivative (i.e. a 2-amino-4-pyrimidone derivative) or a triazine derivative, or a tautomer of these derivatives. More preferably, the nitrogen containing compound is an isocytosine having an alkyl or oligoethylene glycol group in the 6-position, most preferably methyl, or ethylhexyl. The isocyanates or the thioisocyanates can be monofunctional isocyanates or monofunctional thioisocyanates or bifunctional diisocyanates or bifunctional thioisocyanates (for example alkyl or aryl (di)(thio)isocyanate(s)).

A particularly suitable structural element (c) according to the invention are the compounds shown below having general formulae (3) or (4), and tautomers thereof:

(3)

(4)

The structural element (c) according to formulae (3) or (4), respectively, is bonded to the linking moiety (b) at $R_1$, $R_2$ or $R_3$ (so that $R_1$, $R_2$ or $R_3$ represent a direct bond) with the other R groups representing a random side chain or are hydrogen atoms. More preferably, the structural element (c) is bonded to the linking moiety (b) at $R_1$ (so that $R_1$ represents a direct bond) whereas $R_2$ and $R_3$ are a random side chain or are hydrogen atoms. Most preferably, $R_2$ is a random side chain and $R_3$ a hydrogen atom, wherein the random side chain is an alkyl or oligoethylene glycol group in the 6-position, most preferably methyl, or ethylhexyl.

The linking moiety (b) may be all kinds of shorter or longer chains, for example saturated or unsaturated, branched, cyclic or linear alkyl chains, siloxane chains, ester chains, ether chains and any chain of atoms used in traditional polymer chemistry, whether or not substituted with functional groups such as esters, ethers, ureas or urethanes. Preferably, the linking moiety (b) is a $C_1$–$C_{20}$ straight chain or branched alkylene, arylene, alkarylene or arylalkylene group, more preferably a $C_2$–$C_{10}$ straight chain or branched alkylene, arylene, alkarylene or arylalkylene group, wherein the alkylene, arylene, alkarylene or arylalkylene group may be substituted with other groups or may contain cyclic groups as substituent or in the main chain. Examples of such groups are methylene, ethylene, propylene, tetramethylene, pentamethylene, hexamethylene heptamethylene, octamethylene, nonamethylene, 1,6-bis(ethylene) cyclohexane, 1,6-bismethylene benzene, etc. The alkylene, arylene, alkarylene or arylalkylene groups may be interrupted by heteroatoms, in particular heteroatoms selected from the group of oxygen, nitrogen, and sulphur. The linking moiety (b) that links the monomeric unit having a polymerizable group (a) to structural element (c) is derived from a compound that must have at least two functional groups, e.g. hydroxy, carboxylate, carboxylic ester, acyl halide, isocyanate, thioisocyanate, primary amine, secondary amine, or halogen functions. These functional groups are preferably present as end groups. According to the invention, such preferred compounds from which the linking moieties (b) are derived are preferably those having isocyanate or thioisocyanate end groups, more preferably isocyanate end groups. Most preferably, these compounds are diisocyanates or dithioisocyanates, in particular diisocyanates. Examples of suitable diisocyanates that can be used in this invention are:

1,4-diisocyanato-4-methyl-pentane,
1,6-diisocyanato-2,2,4-trimethylhexane,
1,6-diisocyanato-2,4,4-trimethylhexane,
1,5-diisocyanato-5-methylhexane,
3(4)-isocyanatomethyl-1-methylcyclohexyl isocyanate,
1,6-diisocyanato-6-methyl-heptane,
1,5-diisocyanato-2,2,5-trimethylhexane,
1,7-diisocyanato-3,7-dimethyloctane,
1-isocyanato-1-methyl-4-(4-isocyanatobut-2-yl)-cyclohexane,
1-isocyanato-1,2,2-trimethyl-3-(2-isocyanato-ethyl)-cyclopentane,
1-isocyanato-1,4-dimethyl-4-isocyanatomethyl-cyclohexane,
1-isocyanato-1,3-dimethyl-3-isocyanatomethyl-cyclohexane,
1-isocyanatol-n-butyl-3-(4-isocyanatobut-1-yl)-cyclopentane.
1-isocyanato-1,2-dimethyl-3-ethyl-3-isocyanatomethyl-cyclopentane,
3(4)-isocyanatomethyl-1-methylcyclohexyl isocyanate (IMCI),
toluene diisocyanate (TDI),
methylene diphenyl diisocyanate (MDI),
methylene dicyclohexane 4,4-diisocyanate,
isophorone diisocyanate (IPDI), hexane diisocyanate (HDI).

Examples of suitable thioisocyanates are the dithioisocyanate derivatives of the compounds exemplified above for suitable dithiocyanates.

Preferably, the diisocyanate is IPDI, HDI, MDI, TDI or methylene dicyclohexane 4,4-diisocyanate and their thioisocyanate counterparts. According to the invention, however, the diisocyanates are more preferably used than dithioisocyanates.

The monomeric unit having a polymerizable group (a) can be any monomeric unit having a polymerizable group. The monomeric unit having a polymerizable group (a) comprises preferably monomeric units having an ethylenically unsaturated group or an ion-polymerizable group and most preferably the monomeric unit having a polymerizable group comprises a monomeric unit having an ethylenically unsaturated group, i.e. a group derived from monomers having a carbon carbon double bond. According to a preferred embodiment of the invention, the monomeric unit having a polymerizable group has at least one functional group such as hydroxy, carboxylic acid, carboxylic ester, acyl halide, isocyanate, thioisocyanate, primary amine, secondary amine or halogen groups. According to a more preferred embodiment of the invention, the monomeric unit having a polymerizable group is derived from acrylates, methacrylates, acrylamides, methacrylamides, styrenes, vinyl-pyridines, other vinyl monomers, lactones, other cyclic esters, lactams, cyclic ethers and cyclic siloxanes. According to the most preferred embodiment of the invention, the monomeric unit having a polymerizable group is derived from acrylates, methacrylates, acrylamides, methacrylamides and vinyl esters, most preferably vinyl acetates. Examples of compounds from the monomeric units having a polymerizable group that are in particular useful in carrying out the invention are: 2-hydroxyethyl acrylate, 2-hydroxy-propyl acrylate, 2,3-dihydroxypropyl acrylate, poly(ethylene glycol) acrylate, N-hydroxymethyl acrylamide, 2-hydroxyethyl methacrylate, 2-hydroxy-propyl methacrylate, 2,3-dihydroxypropyl methacrylate, poly(ethylene glycol) methacrylate, N,N-dimethylaminoethylmethacrylate, N-hydroxymethyl methacrylamide, vinylacetate, 4-hydroxymethyl-styrene, 4-aminomethyl-styrene, hexahydro-7-oxo-1H-azepine-4-carboxylic acid and 2,3-epoxy-1-propanol.

According to the invention, the monomers are preferably prepared by the following methods.

According to a first method, the monomeric unit having a polymerizable group is reacted in a first step with the compound that must have at least two functional groups. In a subsequent step, the product obtained in the first step is reacted with the nitrogen containing compound. Suitable and preferred structures of the monomeric unit having a polymerizable group, the compound that must have at least two functional groups and the nitrogen containing compound are described above.

According to a second method, the nitrogen containing compound is reacted in a first step with the compound that must have at least two functional groups. In a subsequent step, the product obtained in the first step is reacted with the monomeric unit having a polymerizable group.

According to a third method, the nitrogen containing compound is reacted directly with the monomeric unit having a polymerizable group wherein the monomeric unit is able to form a urea linkage between both reactants.

According to these methods, the monomeric unit having a polymerizable group is most preferably selected from the group of monomeric units having an ethylenically unsaturated group, in particular monomers having a carbon carbon double bond, wherein the monomeric unit having a polymerizable group has preferably at least one functional group, wherein the functional group is selected from the group of hydroxy, carboxylic acid, carboxylic ester, acyl halide, isocyanate, thioisocyanate, primary amine, secondary amine or halogen groups. More preferably, the monomeric unit having a polymerizable group is selected from the group of acrylates, methacrylates, acrylamides, methacrylamides, styrenes, vinyl-pyridines, other vinyl monomers, lactones, other cyclic esters, lactams, cyclic ethers and cyclic siloxanes having a functional group selected from hydroxy, carboxylic acid, carboxylic ester, isocyanate, thioisocyanate, primary amine, secondary amine or halogen groups. Even more preferably, the monomeric unit having a polymerizable group is selected from the group of acrylates, methacrylates, acrylamides, methacrylamides, and vinyl esters, in particular vinyl acetates, said acrylates, methacrylates and vinyl esters having preferably a functional group selected from hydroxy, carboxylic acid, carboxylic ester, acyl halide, isocyanate, thioisocyanate, primary amine, secondary amine or halogen groups.

Preferred embodiments of the methods for the preparation of the monomers are shown below in Schemes 1–3.

Scheme 1 wherein $R_2$ and $R_3$ are as defined above, $R_4$ is hydrogen or methyl, A is a chain, preferably an oligomethylene chain or an oligoethylene glycol chain (as will be understood and appreciated by the person skilled in the art, A may be absent so that the monomeric unit having a polymerizable group has a carboxylic group as functional group. Similarly, instead of the acrylic/methacrylic acid moieties shown in Schemes 1 and 2, their corresponding amide moieties be used) and B is the chain of the linking moiety (b) described above.

Scheme 2

Scheme 3

In Scheme 3 $R_6$ and $R_7$ represent each independently a $C_1$–$C_6$ alkyl group, wherein $R_7$ is preferably methyl.

Description of the Co-Polymerization and of the Polymer

The polymers presented in this invention are obtained by co-polymerizing the monomer containing the 4H-unit with one or more, optionally different comonomers that can be from the same family or from a different family of monomers. These comonomers are preferably selected from the group of: acrylic acid; $C_1$–$C_{30}$ branched or linear alkyl esters of acrylic acid; methacrylic acid; $C_1$–$C_{30}$ branched or linear alkyl esters of methacrylic acid; acrylamides or methacrylamides wherein the amide group may be substituted with one or two $C_1$–$C_{30}$ branched or linear alkyl groups; vinyl esters, preferably vinyl acetates; other compounds having a vinyl group wherein said compounds are preferably selected from pyrrolidones, imidazoles, pyridines, caprolactams, piperidones, benzene and derivatives thereof; $C_4$–$C_{20}$ alkadienes; lactones; lactams; and saturated or unsaturated heterocyclic compounds containing one to five oxygen atoms. Examples of suitable comonomers are acrylic acid, methyl acrylate, butyl acrylate, 2-ethylhexyl acrylate, 2-hydroxyethyl acrylate, N,N-dimethylacrylamide, N-isopropylacrylamide, methacrylic acid, methyl methacrylate, ethyl methacrylate, butyl methacrylate, isobutyl methacrylate, 2-ethylhexyl methacrylate, lauryl methacrylate, 2-hydroxy-ethyl methacrylate, vinylacetate, N-vinylpyrrolidinone, 2-vinylpyridine-1-oxide, N-vinyl imidazole, N-vinyl pyridine, N-vinylcaprolactam, N-vinyl-2-piperidone, acrylonitrile, styrene, butadiene, isoprene, caprolacton, butyrolacton, caprolactam, ethyleneoxide, propyleneoxide, tetrahydrofuran, 3,6-dimethyl-1,4-dioxane-2,5-dione, 1,4-dioxane-2,5-dione.

The copolymerizations may be of any type (for example, bulk, dispersion, solution, emulsion, suspension or inverse phase emulsion) and of any mechanism (for example, radical polymerization, condensation polymerization, transition metal catalyzed polymerization or ring opening polymerization).

The copolymer backbone acquired may be of any type (linear, branched, star, hyperbranched, dendritic, comb-like or the like).

The product copolymer may be of any structure. For example random, regular, tapered or block copolymer structures are allowed.

According to the invention, the molecular weight of the polymers are preferably not too high. A preferred number average molecular weight range is 500–50000.

The copolymers according to the invention are in particular suitable for applications related to personal care (hair preparations, skin cosmetics and laundry aids), surface coatings (leather, textile, optical fibers, paper and paint formulations), imaging technologies (printing, stereolithography, photography and lithography), biomedical applications (materials for controlled release of drugs and materials for tissue-engineering), tablet formulation, adhesive and sealing compositions, and thickening agent and binders.

EXAMPLES

The following examples describe:

(i) the synthesis of building blocks that are needed to synthesize the monomers and polymers that are presented in these examples;

(ii) the synthesis of monomers that contain the 4H hydrogen bonding unit. Easy to produce methacrylates are described, as well as an acrylate monomer and an acrylamide monomer;

(iii) the copolymerization of various 4H bonding containing monomers with monomers such as HEMA (hydroxy ethylmethacrylate) or MMA (methyl methacrylate). Several examples deal with the co-polymerization of three monomers, one of which has a pendant 4H bonding unit. As polymerization techniques, ATRP and AIBN radical polymerization procedures are given. Different molecular weights of polymers are obtained, as well as different levels of incorporation of the 4H hydrogen bonding unit; and

(iv) a comparison between the solution viscosity in chloroform of two PMMA samples of comparable molecular weight: one of the PMMA samples is prepared by ATRP copolymerization of MMA with a monomer containing a 4H-bonding unit, the other sample is PMMA prepared by ATRP homopolymerization of MMA. This example illustrates that properties of polymers—in this case the solution viscosity can be deviated strongly when pending 4H hydrogen bonding units are incorporated.

(i) The Synthesis of Building Blocks

Example 1

Synthesis of an Isocyanate Synthon 1,6-Hexyldiisocyanate (650 g) and methyl-isocytosine (or 2-amino-4-hydroxy-6-methyl-pyrimidine, 65.1 g) were suspended in a 2-liter flask. The mixture was stirred overnight at 100° C. under an argon atmosphere. After cooling to room temperature, a liter of pentane was added to the suspension, while stirring was continued. The product was filtered, washed with pentane and dried in vacuum. A white powder was obtained. $^1$H NMR (400 MHz, CDCl$_3$): δ 13.1 (1H), 11.8 (1H), 10.1 (1H), 5.8 (1H), 3.3 (4H), 2.1 (3H), 1.6 (4H), 1.4 (4H). IR (neat): ν 2935, 2281, 1698, 1668, 1582, 1524, 1256.

Example 2

Synthesis of the ATRP Initiator Benzyl 2-bromo-2-methyl-propionate

2-Bromo-2-methylpropionyl bromide (6.8 mL) was diluted with dichloromethane and added to a solution of triethylamine (7.7 mL) and benzyl alcohol (4.8 mL), while the mixture was cooled in an ice bath and while maintaining an argon atmosphere. The solution was stirred for one hour at 0° C. and then overnight at room temperature. Volatiles were evaporated and the residue was treated with diethyl-ether. The formed salt was removed by filtration and the filtrate was washed with an HCl solution and with water. The ether solution was dried with MgSO$_4$ and concentrated to yield a yellowish liquid. Silica column chromatography using a 2/1 hexane/ethyl acetate mixture as eluent gave a colourless transparent liquid. $^1$H NMR (400 MHz, CDCl$_3$): δ 7.4 (5H), 5.3 (2H), 2.0 (6H).

Example 3

Synthesis of 6-(1-ethylpentyl)-isocytosine

Potassium ethyl malonate (150 g) and acetonitrile (1.4 L) were stirred in a flask and brought to a temperature of 10–15° C. Triethylamine (132 mL) was added drop wise, while keeping the mixture under an argon atmosphere. Dried MgCl$_2$ (101.6 g) was added and the suspension was stirred for 2 hours at room temperature. Thereafter, the suspension was cooled to 0° C. and 2-ethylhexanoyl chloride (74 mL) was added drop wise, and the mixture was allowed to warm up to room temperature and was stirred overnight. The acetonitrile was removed by evaporation, 400 mL toluene was added and evaporated, 700 mL of toluene was added and the mixture was cooled to 10° C. An aqueous HCl solution was added slowly, and the organic layer was separated, washed with an HCl solution and then with a bicarbonate solution. The organic layer was dried with Na$_2$SO$_4$ and concentrated to give the β-ketoester as a liquid. The β-ketoester (50 g) and guanidine carbonate (49.8 g) were boiled in ethanol (300 mL) for two days using a Soxhlett set-up with molsieves in the thimble. The suspension was filtered, ethanol was evaporated and the product was dissolved in chloroform. After washing with a bicarbonate solution, the organic layer was dried with MgSO$_4$, concentrated and dropped into an excess of pentane to yield a white powder. $^1$H NMR (400 MHz, CDCl$_3$): δ 11.6–10.6 (1H), 7.6–6.6 (2H), 5.6 (1H), 2.2 (1H), 1.5 (4H), 1.2 (4H), 0.8 (6H). IR (neat): ν 3322, 3152, 2929, 2860, 1635, 1463, 1378, 1582, 1524.

(ii) Synthesis of 4H Hydrogen Bonding Unit Containing Monomers

Example 4

Monomer 1, a 4H Hydrogen Bonding Unit Containing Methacrylate Monomer monomer 1

The isocyanate (79 g) was suspended in chloroform (1.5 L), and thereafter hydroxy ethyl methacrylate (HEMA, 64 mL) and 15 drops of dibutyl tin dilaurate (DBTDL) were added. The mixture was stirred at an oil bath temperature of 90° C. for 4 hours, and was then cooled and filtered. The filtrate was concentrated and dropped into an excess of diethylether. The white precipitate was collected by filtration, and was washed with diethylether. Drying in vacuo gave a white solid product (90 g). $^1$H NMR (400 MHz, CDCl$_3$): δ 13.1 (1H), 11.8 (1H), 10.1 (1H), 6.1 (1H), 5.8 (1H), 5.6 (1H), 5.0 (1H), 4.3 (4H), 3.3–3.2 (4H), 2.1 (3H), 1.9 (3H), 1.7–1.2 (8H). IR (neat): ν 3301, 2932, 1720, 1699, 1685, 1665, 1582, 1525, 1258.

Example 5

Monomer 2, a 4H Hydrogen Bonding Unit Containing Acrylate Monomer column chromatography using ethyl acetate/hexane yielded a light yellowish waxy solid. $^1$H NMR (400 MHz, CDCl$_3$): δ 13.1 (1H), 12.0 (1H), 10.5 (1H), 6.2 (1H), 5.8 (1H), 5.6 (1H), 4.3 (2H), 3.6 (2H), 2.3 (1H), 1.9 (3H), 1.8–1.5 (4H), monomer 2

The isocyanate (46 g) was suspended in chloroform (1 L), and thereafter hydroxy ethyl acrylate (HEA, 36 mL) and 10 drops of dibutyl tin dilaurate (DBTDL) were added. The mixture was stirred at an oil bath temperature of 90° C. for 4 hours, and was then cooled and filtered. The filtrate was concentrated and an excess of diethylether was added. The white precipitate was collected by filtration, and was washed with diethylether. Drying in vacuo gave a white solid product. $^1$H NMR (400 MHz, CDCl$_3$): δ 13.1 (1H), 11.8 (1H), 10.1 (1H), 6.5 (1H), 6.2 (1H), 5.9 (2H), 5.1 (1H), 4.4 (4H), 3.3 (2H), 3.2 (2H), 2.1 (3H), 1.7–1.3 (8H). IR (neat): ν 3307, 2928, 1725, 1702, 1682, 1664, 1584, 1548, 1258, 1192.

Example 6

Monomer 3, a 4H Hydrogen Bonding Unit Containing Methacrylate Monomer monomer 3

2-Isocyanatoethyl methacrylate (7.0 mL) was added to a solution of 6-(1-ethylpentyl)isocytosine (13.4 g) in dry pyridine (150 mL). The reaction mixture was stirred under an argon atmosphere at 80° C. for 4 hrs. The product was isolated by evaporation of the solvent, and subsequent filtration over silica using chloroform/methanol (4%). Silica 1.4–1.2 (4H), 0.9 (6H). IR (neat): ν 2959, 2930, 1720, 1697, 1645, 1582, 1555, 1525, 1462, 1254, 1160.

Example 7

Monomer 4, a 4H Hydrogen Bonding Unit Containing Methacrylate Monomer monomer 4

The PEG-MA monomer (an average molecular weight of 306; 2.2 g), the isocyanate (1.8 g) and a few drops of DBTDL were boiled overnight in chloroform. Hexane was added to cause precipitation. The product was isolated by filtration, washing with hexane and with diethyl ether. $^1$H NMR (400 MHz, CDCl$_3$): δ 13.1 (1H), 11.8 (1H), 10.1 (1H), 7.2 (1H), 6.0 (1H), 5.7 (1H), 5.6 (1H), 4.2 (2H), 4.0 (2H), 3.7 (2H), 3.6–3.4 (15H-20H), 3.1 (2H), 2.9 (2H), 2.1 (3H), 1.9 (3H), 1.4 (4H), 1.2 (4H).

Example 8

Monomer 5, a 4H Hydrogen Bonding Unit Containing Acrylamide Monomer monomer 5

The isocyanate (1 g) was dissolved in 5 mL of acrylic acid and heated to 70° C. The mixture was stirred under an argon atmosphere. Copper(II)acetate (8 mg) was added and heating at 70° C. was maintained for 2 days. The product was obtained by precipitation of the reaction mixture into diethylether. The solid was isolated by filtration, and was dissolved in chloroform. The organic solution was washed with a bicarbonate solution and dried with Na$_2$SO$_4$. Filtration and concentration of the filtrate gave a white powder. $^1$H NMR (400 MHz, CDCl$_3$): δ 13.1 (1H), 11.8 (1H), 10.1 (1H), 6.4–6.0 (3H), 5.8 (1H), 5.6 (1H), 3.4–3.2 (4H), 2.1 (3H), 1.7–1.2 (8H). IR (neat): ν 3278, 2935, 1699, 1665, 1652, 1582, 1525.

(iii) Co-Polymerizations

ATRP (Atom Transfer Radical Polymerization) Procedures Typical A TRP Co-Polymerization Experiment

A 25 mL round bottom flask containing the appropriate amounts of CuBr, bipyridine and 4H hydrogen bonding unit containing monomer was degassed (de-oxygenated) by vacuum followed by argon backfill, and repeating this cycle twice. The other monomer(s) and the solvent were degassed (de-oxygenated) by bubbling through argon for at least 45 minutes prior to addition of these liquids to the 25 mL flask by use of a syringe. The reaction mixture was stirred until all components had dissolved (sometimes after short warming) to produce a homogeneous dark brown solution. The reaction flask was placed in a water bath that was maintained at room temperature, and finally, the ATRP-initiator was added using a syringe. Polymerization occurred immediately, leading to an increase in viscosity of the reaction mixture.

Samples were taken at regular intervals to assess the extent of polymerization by $^1$H NMR spectroscopy. On exposure to air, the dark brown sample solutions turned blue, indicating aerial oxidation of Cu(I) to Cu(II). After the polymerization was complete, the polymer was recovered by precipitation into an appropriate non-solvent.

The applied ATRP polymerization procedure allows that $^1$H NMR spectroscopy can be used to determine certain features of the isolated polymer: the M$_n$ of the polymer can be determined by comparing the integral of the benzylic signals of the polymer end group to the integral of the monomeric unit signals. Additionally, $^1$H NMR can be used to calculate the average number of 4H hydrogen bonding units per polymer chain by considering the integral of the benzylic signals of the polymer end group and the integral of the alkylidene signal of the 4H hydrogen bonding unit.

Example 9

PHEMA with Pendant 4H Hydrogen Bonding Units by ATRP Copolymerization of HEMA and Monomer 1 monomer 1

A 25 mL round bottom flask containing 0.14 g of CuBr, 0.354 g of bipyridine, and 0.853 g of monomer 1 were degassed by vacuum followed by argon backfill (3 times). Degassed DMSO (4.7 mL) and hydroxyethylmethacrylate (HEMA, 4.7 mL) were added via a syringe. The reaction flask was placed in a water bath at room temperature and stirred to produce a dark brown solution. Finally, 0.255 g of initiator was added prompting immediate polymerization. After half an hour of reaction, the polymer was recovered by precipitation into chloroform and drying of the precipitate.

$^1$H NMR analysis verified that monomer 1 was co-polymerized into the polymer product: it showed that the co-polymerization produced PHEMA with a molecular weight $M_n$ of approximately 10 kD and with ca. 1.7 pendant 4H hydrogen bonding units per polymer chain. $^1$H NMR (400 MHz, DMSO-$d_6$): δ 7.4 (phenyl), 5.8 (alkylidene monomer 1), 5.1 (benzylic methylene), 3.9, 3.6, 2.1 (methyl monomer 1), 2.0–0.6.

Example 10

PHEMA with Pendant 4H Hydrogen Bonding Units by ATRP Co-Polymerization of HEMA, PEG-MA and Monomer 3

A 25 mL round bottom flask containing 0.31 g of CuBr, 0.70 g of bipyridine and 1.51 g of monomer 3 was degassed by vacuum followed by argon backfill (3 times). Degassed DMSO (5 mL), hydroxyethylmethacrylate (HEMA, 5 mL) and polyethyleneglycol methacrylate (PEG-MA, $FW_{average}$=306, 1.14 g) were added via a syringe. The reaction flask was placed in a water bath at room temperature and stirred to produce a dark brown solution. Finally, 0.56 g of initiator was added prompting immediate polymerization. After half an hour of reaction, the polymer was recovered by precipitation into an EDTA (25 g/L) solution in water and drying of the precipitate. Yield: 6.25 g.

$^1$H NMR analysis verified that monomer 3 was co-polymerized into the polymer product: it showed that the co-polymerization produced PHEMA with a molecular weight $M_n$ of approximately 5 kD and with 1.5–2.0 pendant 4H hydrogen bonding units per polymer chain. SEC (0.01 M LiBr in DMF) showed an $M_n$ of 18 kD and a polydispersity of D=1.8, as compared to polystyrene standards. Polystyrene does not dissolve well in the used eluent, so these numbers are overrated. $^1$H NMR (400 MHz, DMSO-$d_6$): 7.4 (phenyl), 5.8 (alkylidene monomer 3), 5.1 (benzylic methylene), 3.9, 3.7–3.2, 2.0–0.6.

Example 11

PHEMA with Pendant 4H Hydrogen Bonding Units by ATRP Co-Polymerization of HEMA, PEG-MA and Monomer 3

A 25 mL round bottom flask containing 0.144 g of CuBr, 0.272 g of bipyridine and 0.70 g of monomer 3 was degassed by vacuum followed by argon backfill (3 times). Degassed DMSO (5 mL), hydroxy ethylmethacrylate (HEMA, 5 mL) and polyethyleneglycol methacrylate (PEG-MA, $FW_{average}$=306, 0.55 mL) were added via a syringe. The reaction flask was placed in a water bath at room temperature and stirred to produce a dark brown solution. Finally, 0.254 g of initiator was added prompting immediate polymerization. After 35 minutes of reaction, the polymer was recovered by precipitation into an EDTA (25 g/L) solution in water and drying of the precipitate. Yield: 5.75 g.

$^1$H NMR analysis verified that monomer 3 was co-polymerized into the polymer product: it showed that the co-polymerization produced PHEMA with a molecular weight $M_n$ of approximately 10 kD and with ca. 2.5 pendant 4H hydrogen bonding units per polymer chain. SEC (0.01 M LiBr in DMF) showed an $M_n$ of 27 kD and a polydispersity of D=1.6, as compared to polystyrene standards. Polystyrene does not dissolve well in the used eluent, so these numbers are overrated. $^1$H NMR (400 MHz, DMSO-$d_6$): δ 7.4 (phenyl), 5.8 (alkylidene monomer 3), 5.1 (benzylic methylene), 3.9, 3.7–3.2, 2.0–0.6.

Example 12

PHEMA with Pendant 4H Hydrogen Bonding Units by ATRP Co-Polymerization of HEMA and Monomer 3

A 25 mL round bottom flask containing 0.062 g of CuBr, 0.179 g of bipyridine and 0.60 g of monomer 3 was degassed by vacuum followed by argon backfill (3 times). Degassed DMSO (2 mL) and hydroxyethylmethacrylate (HEMA, 2 mL) were added via a syringe. The reaction flask was placed in a water bath at room temperature and stirred to produce a dark brown solution. Finally, 0.114 g of initiator was added prompting polymerization. After 35 minutes of reaction, the polymer was recovered by precipitation into an EDTA (25 g/L) solution in water and drying of the precipitate.

$^1$H NMR analysis verified that monomer 3 was co-polymerized into the polymer product: it showed that the co-polymerization produced PHEMA with an $M_n$ of ca. 10 kD and with ca. 3.5–4.0 pendant 4H hydrogen bonding units per polymer chain. $^1$H NMR (400 MHz, DMSO-$d_6$): δ 7.4 (phenyl), 5.8 (alkylidene monomer 3), 5.1 (benzylic methylene), 3.9, 3.7–3.2, 2.0–0.6.

Example 13

PHEMA with Pendant 4H Hydrogen Bonding Units by ATRP Co-Polymerization of HEMA and Monomer 4 monomer 4

R =

A 25 mL round bottom flask containing 0.062 g of CuBr, 0.134 g of bipyridine and 0.51 g of monomer 4 was degassed by vacuum followed by argon backfill (3 times). Degassed DMSO (2 mL) and hydroxyethylmethacrylate (HEMA, 2 mL) were added via a syringe. The reaction flask was placed in a water bath at room temperature and stirred to produce a dark brown solution. Finally, 0.115 g of initiator was added prompting immediate polymerization. After half an hour of reaction, the polymer was recovered by precipitation into an EDTA (25 g/L) solution in water and drying of the precipitate.

$^1$H NMR analysis verified that monomer 4 was co-polymerized into the polymer product: it showed that the co-polymerization produced PHEMA with a molecular weight $M_n$ of approximately 6–7 kD and with ca. 1.5 pendant 4H hydrogen bonding units per polymer chain. $^1$H NMR (400 MHz, DMSO-$d_6$): δ 7.4 (phenyl), 7.2 (amide monomer 4) 5.8 (alkylidene monomer 4), 5.1 (benzylic methylene), 3.9, 3.7–3.2, 2.20.6.

Example 14

PMMA with Pendant 4H Hydrogen Bonding Units by ATRP Co-Polymerization of MMA and Monomer 3

A 25 mL round bottom flask containing 0.134 g of CuBr and 0.51 g of monomer 3 was degassed by vacuum followed by argon backfill (3 times). Degassed toluene (5 mL) and methyl methacrylate (MMA, 5 mL) were added via a syringe. The mixture was stirred at 60° C. to acquire a homogeneous solution. Pentamethyldiethylene triamine (PMDETA, 0.20 mL) was added, so that a light green solution was obtained. Finally, 0.185 mL of ATRP initiator was added prompting polymerization. After 150 minutes, the reaction mixture was diluted in chloroform and filtered over silica. The filtrate was concentrated, dissolved in toluene and precipitated into hexane.

$^1$H NMR analysis verified that monomer 3 was copolymerized into the polymer product: it showed that the co-polymerization produced PMMA with a molecular weight $M_n$ of approximately 11 kD and with ca. 2.0–2.5 pendant 4H hydrogen bonding units per polymer chain. SEC (chloroform) showed an $M_n$ of 12.5 kD and a dispersity of D=1.6 (data versus polystyrene standards). $^1$H NMR (400 MHz, CDCl$_3$): δ 13.1 (monomer 3), 12.1 (monomer 3), 10.5 (monomer 3), 7.4 (phenyl), 5.9 (alkylidene monomer 3), 5.1 (benzylic methylene), 4.1 (monomer 3), 3.7–3.5, 2.1–1.6, 1.2–0.8.

Example 15

PMMA by ATRP Polymerization of MMA

A 25 mL round bottom flask containing 0.138 g of CuBr was degassed by vacuum followed by argon backfill (3 times). Degassed methyl methacrylate (MMA, 5.2 mL) was added via a syringe. Then pentamethyldiethylene triamine (PMDETA, 0.20 mL) was added, and the mixture was stirred and brought to 60° C. Finally, 0.185 mL of ATRP initiator was added prompting polymerization. After 30 minutes, the reaction mixture was diluted in chloroform and filtered over silica. The filtrate was concentrated, dissolved in toluene and precipitated into hexane.

$^1$H NMR (400 MHz, CDCl$_3$): δ 7.4 (phenyl), 5.1 (benzylic methylene), 3.7–3.5, 2.1–1.7, 1.6–0.8. $^1$H NMR analysis showed that PMMA with a molecular weight $M_n$ of approximately 11 kD was prepared. SEC (chloroform) showed an $M_n$ of 15 kD and a dispersity of D=1.45 (data versus polystyrene standards).

AIBN Radical Polymerization Procedures

Typical Procedure

A solution of HEMA, 4H hydrogen containing monomer, AIBN and transfer agent in DMF was degassed by purging with argon for 1 hr prior to polymerization was commenced. After the reaction time at a certain temperature, the mixture was cooled down to room temperature and the polymer was recovered by precipitation into an appropriate non-solvent, filtration and drying.

Example 16

PHEMA with Pendant 4H Hydrogen Bonding Units by AIBN Radical Co-Polymerization of HEMA and Monomer 3

A mixture of HEMA (4.7 mL), monomer 3 (0.725 g), DMF (30 mL), mercaptoethanol (0.02 mL) and AIBN (11.3 mg) in a dropping funnel was degassed by bubbling through of argon for an hour. Then, the mixture was dropped into a flask that was immersed in an oil bath of 60° C. After addition, the mixture was stirred for two days. After one day a second batch of AIBN (11.3 mg) was added The polymer was precipitated into THF/hexane 3:1 and dried in a vacuum stove. NMR verified that monomer 3 was co-polymerized into the polymer product. $^1$H NMR (400 MHz, DMSO-d$_6$): δ 5.8 (alkylidene monomer 3), 4.0–3.8, 3.7–3.4, 2.0–0.6.

Example 17

PHEMA with Pendant 4H Hydrogen Bonding Units by AIBN Radical Co-Polymerization of HEMA and Monomer 3

In a mixture of HEMA (5 mL), monomer 3 (0.4 g), DMF (15 mL), mercaptoethanol (0.060 mL) and AIBN (12 mg) in a flask were degassed by bubbling through of argon for an hour. Then, the flask was immersed in an oil bath of 80° C. for 4 hours. The polymer was precipitated into THF/hexane 3:1 and dried in a vacuum stove. SEC with UV-detection verified that monomer 3 was co-polymerized into the polymer product. Other SEC data (0.01 M LiBr in DMF), $M_n$=24 kD, D=1.4, data versus polystyrene standards.

Example 18

Solution Viscosity Measurements

Figure 1:
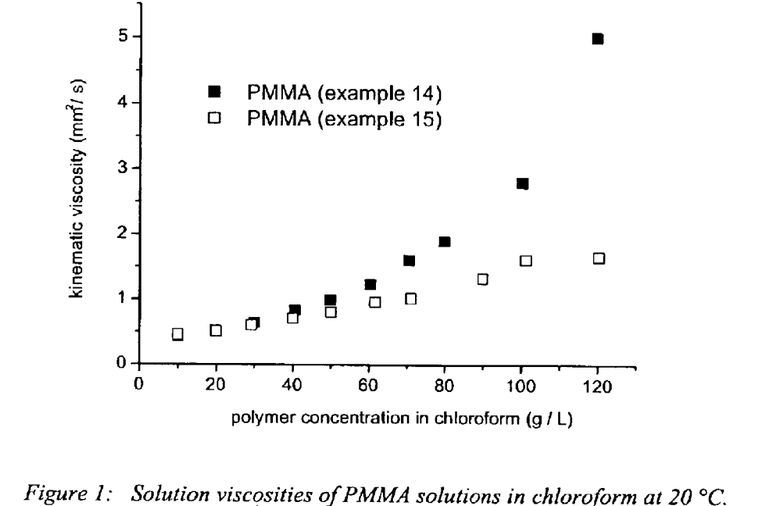
FIG. 1. Solution viscosities of PMMA solutions in chloroform at 20° C.

The PMMA polymers prepared by ATRP polymerization that have been described in examples 14 and 15 are of approximately the same molecular weight as $^1$H NMR and SEC analyses attest. The only difference between the PMMA polymers is that the one described in example 14 has pending 4H hydrogen bonding units. FIG. 1 depicts the solution viscosities of PMMA solutions in chloroform at 20° C.

The solution (kinematic) viscosity of the PMMA with pending 4H hydrogen bonding units is much more dependent on the concentration as that of the regular PMMA. The difference is caused by extra 4H hydrogen bonding interactions between the PMMA chains. This example illustrated that the introduction of 4H hydrogen bonding units to polymers can drastically alter the behavior of these polymers, giving rise to unique properties.

What is claimed is:

1. A monomer comprising (a) a monomeric unit having a group that can be polymerized, a linking moiety (b) and a structural element (c) capable of forming at least four hydrogen bridges, wherein the monomer has the general structure (a)-(b)-(c), and wherein the linking moiety (b) forms a chemical bond with the structural element (c), which bond is not a carbon—carbon single bond.

2. The monomer according to claim 1, wherein the structural element (c) has the general form (1') or (2'):

(1')

-continued (2')

wherein n≧4 and the C—X$_i$(i=1–n) and the C—Y$_i$(i=1–n) linkages each represent a single or double bond and X$_i$ represent donors or acceptors that form hydrogen bridges with the H-bridge forming monomer unit containing a corresponding general form (2') linked to them with X$_i$ representing a donor and Y$_i$ an acceptor or vice versa.

3. The monomer according to claim 2, wherein n=4 and wherein X$_1$ and X$_2$ are donors or acceptors, respectively, and X$_3$ and X$_4$ are donors or acceptors, respectively.

4. The monomer according to claim 2, wherein the donors and acceptors are O, S, and N atoms.

5. The monomer according to claim 2, wherein the structural element (c) has the general formula (3) or (4), or tautomers thereof:

(3)

(4)

wherein the structural element (c) is bonded to the linking moiety (b) at R$_1$, R$_2$ or R$_3$ (so that R$_1$, R$_2$ or R$_3$ represent a direct bond) with the other R groups representing a random side chain or are hydrogen atoms.

6. A process for the preparation of a monomer as defined in claim 1, wherein a monomeric unit having a polymerizable group is reacted in a first step with a compound having at least two functional groups and wherein the product obtained in the first step is reacted with a nitrogen containing compound.

7. A process for the preparation of a monomer as defined in claim 1, wherein a nitrogen containing compound is reacted in a first step with a compound having at least two functional groups and wherein the product obtained in the first step is reacted with a monomeric unit having a polymerizable group.

8. A copolymer comprising the monomer as defined in claim 1 and at least one comonomer.

9. The copolymer according to claim 8, wherein the comonomer is selected from the group of: acrylic acid; $C_1$–$C_{30}$ branched or linear alkyl esters of acrylic acid; methacrylic acid; $C_1$–$C_{30}$ branched or linear alkyl esters of methacrylic acid; acrylamides or methacrylamides wherein the amide group may be substituted with one or two $C_1$–$C_{30}$ branched or linear alkyl groups; vinyl esters; compounds having a vinyl group $C_4$–$C_{20}$ alkadienes; lactones; lactams; and saturated or unsaturated heterocyclic compounds containing one to five oxygen atoms.

10. The copolymer according to claim 8, wherein the copolymer is a linear, branched, star, hyperbranched, dendritic or comb-like copolymer.

11. The copolymer according to claim 8, wherein the copolymer has a random, regular, tapered or block structure.

12. A process for the preparation of a copolymer, wherein a monomer as defined in claim 1 is polymerized with at least one comonomer.

13. The process according to claim 12, wherein the process is conducted in bulk, dispersion, solution, emulsion, suspension or inverse phase emulsion.

14. The monomer according to claim 1, wherein the polymerizable group is an ethylenically unsaturated group.

15. The monomer according to claim 1, wherein the linking moiety (b) has at least one functional group selected from the group consisting of hydroxy, carboxylates, carboxylic esters, acyl halides, isocyanate, thioisocyanate, primary amines, secondary amines, and halogen groups.

16. The monomer according to claim 1, wherein the functional groups are end groups.

17. The monomer according to claim 1, wherein the linking moitey (b) is selected form the group consisting of $C_1$–$C_{20}$ straight chain or branched alkylene, arylene, alkarylene and arylalkylene groups.

18. The copolymer according to claim 9, wherein the vinyl ester is a vinyl acetate.

19. The copolymer according to claim 9, wherein the compounds having a vinyl group are selected from the group consisting of pyrrolidones, imidazoles, pyridines, caprolactams, piperidones, benzene and derivatives thereof.

20. The monomer according to claim 1, wherein the bond is a bond is an ester bond.

21. The monomer according to claim 1, wherein the bond is a bond is an amide bond.

22. The monomer according to claim 1, wherein the bond is a bond is an ether bond.

23. The monomer according to claim 1, wherein the bond is a cabamate bond.

24. The monomer according to claim 1, wherein the bond is a urethane bond.

* * * * *